(12) United States Patent
Shimada et al.

(10) Patent No.: US 9,468,376 B2
(45) Date of Patent: Oct. 18, 2016

(54) OPHTHALMOLOGIC APPARATUS

(71) Applicant: CANON KABUSHIKI KAISHA, Tokyo (JP)

(72) Inventors: Yasuhiro Shimada, Sagamihara (JP); Masato Yajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 301 days.

(21) Appl. No.: 14/065,212

(22) Filed: Oct. 28, 2013

(65) Prior Publication Data

US 2014/0118695 A1   May 1, 2014

(30) Foreign Application Priority Data

Oct. 30, 2012   (JP) ................... 2012-239285

(51) Int. Cl.
*A61B 3/10* (2006.01)
*A61B 3/14* (2006.01)

(52) U.S. Cl.
CPC .................. *A61B 3/14* (2013.01); *A61B 3/102* (2013.01); *A61B 3/1015* (2013.01)

(58) Field of Classification Search
USPC ....... 351/200, 205, 206, 207, 208, 209, 211, 351/221, 222, 243, 245, 246
See application file for complete search history.

(56) References Cited

U.S. PATENT DOCUMENTS

| | | | |
|---|---|---|---|
| 6,925,710 | B1 | 8/2005 | Scalf et al. |
| 7,079,299 | B1 | 7/2006 | Conant et al. |
| 2006/0050421 | A1* | 3/2006 | Ealey ................ G02B 26/0825 359/849 |
| 2011/0279778 | A1 | 11/2011 | Saito |
| 2012/0140171 | A1* | 6/2012 | Hirose ................ A61B 3/1025 351/206 |
| 2012/0154746 | A1 | 6/2012 | Nozato |
| 2012/0250129 | A1* | 10/2012 | Nakatani ........... G02B 26/0841 359/200.6 |

FOREIGN PATENT DOCUMENTS

| | | |
|---|---|---|
| CN | 101196613 A | 6/2008 |
| JP | 2005224327 A | 8/2005 |
| JP | 2007-021044 A | 2/2007 |
| JP | 2012130444 A | 7/2012 |

OTHER PUBLICATIONS

Silvestre Manzanera, et al., "MEMS Segmented-Based Adaptive Optics Scanning Laser Ophthalmoscope", Biomedical Optics Express, May 1, 2011, vol. 2, No. 5, Optical Society of America.
S He, et al., "Repulsive-Force Out-of-Plane Large Stroke Translation Micro Electrostatic Actuator", J. Micromech. Microeng. 21, 2011, IOP Publishing Ltd.
Marco Lombardo, et al., "Adaptive Optics Technology for High-Resolution Retinal Imaging", Sensors 2013, Dec. 27, 2012, vol. 13, pp. 334-366.
Doble et al., "Requirements for discrete actuator and segmented wavefront correctors for aberration compensation in two large populations of human eyes", Applied Optics, Jul. 10, 2007, pp. 4501-4514, vol. 46, No. 20.

* cited by examiner

*Primary Examiner* — Joseph P Martinez
*Assistant Examiner* — Brandi Thomas
(74) *Attorney, Agent, or Firm* — Canon U.S.A. Inc., IP Divison (57) ABSTRACT

An ophthalmologic apparatus includes an aberration measuring unit configured to measure wavefront aberration of returning light, and a reflective optical modulation device configured to modulate the returning light. A control unit controls the reflective optical modulation device to correct the wavefront aberration of the returning light based on a measurement result of the aberration measuring unit. The reflective optical modulation device includes a reflection mirror of which the diameter of an effective region (effective diameter) that reflects the measurement light or the returning beam is 7.5 mm or less, and 61 or more actuators that act on the reflection mirror within the effective diameter. Each of the actuators includes an interdigital electrode having a maximum displacement of 7.5 μm or more.

22 Claims, 7 Drawing Sheets

OPHTHALMOLOGIC APPARATUS

BACKGROUND OF THE INVENTION

1. Field of the Invention

The present invention generally relates to an ophthalmologic apparatus capable of capturing an image of an ocular fundus, and in particular it relates to an ophthalmologic apparatus that includes an adaptive optical system.

2. Description of the Related Art

A scanning laser ophthalmoscope (SLO) is a well know example of an ophthalmologic imaging apparatus. To obtain an image of an ocular fundus with an SLO, an eye is irradiated with laser light in a two-dimensional pattern and the light reflected from the ocular fundus is received by an optical detector to form an image. Further, an imaging apparatus that utilizes interference of low coherence light has been developed as an ophthalmologic imaging apparatus. Such imaging apparatus that utilizes interference of low coherence light is called an optical coherence tomography (OCT) apparatus and is used, in particular, to capture a tomographic image of an ocular fundus or the vicinity thereof. Various OCT systems have been developed including a time domain (TD) OCT system and a spectral domain (SD) OCT system. In particular, in recent years, higher resolution has been achieved in an ophthalmologic imaging apparatus with an increase in the numerical aperture (NA) of an irradiating laser.

When an image of an ocular fundus is to be captured, the image needs to be captured through optical tissues within the eye, such as the cornea and the crystalline lens. Thus, as the resolution is increased, an aberration that occurs in the cornea and crystalline lens increasingly affects the quality of a captured image.

Accordingly, research has been carried out on adaptive optics (AO) SLO and AO-OCT, in which the function of the AO that measures the aberration of an eye and corrects the aberration is integrated into an optical system. For example, in an article entitled "Requirements for discrete actuator and segmented wavefront correctors for aberration compensation in two large populations of human eyes, N. Doble et al., Applied Optics, Vol. 46, No. 20, 10 Jul. 2007, discusses an example of AO-OCT. In AO-SLO or AO-OCT, changes in the wavefront of light incident on an eye is typically measured by a Shack-Hartmann wavefront sensor system. In the Shack-Hartmann wavefront sensor system, measurement light enters an eye, and the reflected light thereof is received by a charge-coupled device (CCD) camera through a micro-lens array, to thereby measure the wavefront of the reflected light. Since the optical tissues within the eye cause aberrations on the wavefront of the light, a reflective optical modulation device is driven to correct the aberrations of the measured wavefront, and an image of the ocular fundus is captured through the reflective optical modulation device. Thus, AO-SLO or AO-OCT can capture the image at high resolution.

There are several types of reflective optical modulation devices including a variable shape mirror and a reflective liquid crystal device. Since the reflective liquid crystal device modulates polarization directions and thus requires two optical elements, which leads to an increase in size of the optical system. Furthermore, because of its high wavelength dependence, the reflective liquid crystal device is not suitable for observation at multiple wavelengths, which is often employed in the observation of an ocular fundus. Thus, a variable shape mirror is preferably used as the reflective optical modulation device.

The variable shape mirror corrects the wavefront by deforming the mirror shape and thus by generating an optical path length difference within the effective diameter in the optical axis direction. Here, a difference in coordinates, in the optical axis direction, of two positions on the mirror surface within the effective diameter is referred to as a displacement amount. Since a mirror is a reflective element, a required maximum displacement amount is half a maximum optical path length to be corrected.

There are various types of variable shape mirrors. Specifically, there is a mirror having a continuous mirror surface that is caused to deform by a plurality of actuators. There is also a segmented mirror that is formed of multiple segments, and the segments are independently driven by respective actuators to be translated in the optical axis direction. There is another type of segmented mirror that is formed of multiple segments, and the segments can be independently driven by respective actuators to be translated in the optical axis direction and tilted about two axes.

Japanese Patent Application Laid-Open No. 2005-224327 discusses a technique in which reflected light from an ocular fundus that includes an aberration is corrected by using at least two reflective optical modulation devices in order to increase the correction amount.

Japanese Patent Application Laid-Open No. 2007-21044 discusses a finding that correction of an aberration of a light flux incident on a model eye using an 85-segmented reflective optical modulation device having a diameter of 12 mm and a maximum displacement amount of 16 µm has resulted in a residual aberration RMS of 0.093 µm. However, Japanese Patent Application Laid-Open No. 2007-21044 does not discuss the number of mirror segments within the effective diameter.

N. Doble et al., Applied Optics, Vol. 46, No. 20, 10 Jul. 2007 discusses a relationship between a Strehl ratio, which indicates the accuracy of the wavefront correction, and the number of actuators for driving the reflective optical modulation device, and a displacement amount of each actuator required for correcting an aberration of a human eye.

Early detection of a progressive disease in an ocular fundus is important. Thus, there is a need for an observation apparatus that is capable of detailed observation at the visual cell level. Visual cells include two types of cells, namely a cone cell having a size of approximately 2 µm to 5 µm and distributed around the macular area, and a rod cell having a size of approximately 2 µm and primarily distributed outside the macular area. A cone cell has a small size of approximately 2 µm in the central fovea in the macular area. Accordingly, detecting an ocular fundus disease at an early stage requires the resolution of approximately 2 µm.

As stated above, an ophthalmologic apparatus into which the function of an adaptive optical system is integrated in order to achieve higher resolution has been developed. However, since eyes to be examined have individual differences in the optical aberration, there has been an issue that a clear image of the visual cells cannot be obtained depending on an eye to be examined.

Although Japanese Patent Application Laid-Open No. 2005-224327 discusses a technique for obtaining a desired correction amount by us ing a plurality of variable shape mirrors, such a technique makes it difficult to obtain a compact optical system.

Although Japanese Patent Application Laid-Open No. 2007-21044 discusses a finding that the aberration has been corrected to the residual aberration RMS of 0.093 µm by using a single variable shape mirror, this residual aberration amount cannot bring the Strehl ratio to 0.8 or less, and thus sufficient optical performance cannot be secured.

SUMMARY OF THE INVENTION

The present invention is directed to an ophthalmologic apparatus having optical performance capable of detailed observation at the visual cell level and including an optical system that is reduced in size.

According to an aspect of the present invention, an ophthalmologic apparatus that is configured to obtain an image of an eye to be examined includes: an aberration measuring unit configured to measure aberration in the eye; a reflective optical modulation device configured to modulate at least one of a measurement light and the returning light; and a control unit configured to control the reflective optical modulation device to correct the wavefront aberration of the returning light based on a measurement result of the aberration measuring unit. The reflective optical modulation device includes a reflection mirror having an effective diameter of 7.5 mm or less and 61 or more actuators that act on the reflection mirror within the effective diameter. Each of the actuators has a maximum displacement of 7.5 μm or more.

Further features of the present invention will become apparent from the following description of exemplary embodiments with reference to the attached drawings.

DESCRIPTION OF THE EMBODIMENTS

A reflective optical modulation device includes a reflection mirror and a plurality of actuators disposed in an in-plane direction of the reflection mirror. The reflection mirror deforms in the optical axis direction as each of the actuators acts on a specific area of the reflection mirror. In order to reproduce a desired shape, the number of actuators and the stroke amount of each actuator need to be increased. This is because the spatial frequency of the Zernike mode increases at higher orders, and thus the number of actuators needs to be increased accordingly.

With an assumption that the resolution at which an ocular fundus is to be observed is equivalent to a beam spot diameter $\omega 1$ at the ocular fundus, the resolution is expressed through the following expression using an incident beam diameter $\omega 0$, a wavelength $\lambda$, and a focal distance f of the eye. $\omega 1 = \omega 0 \cdot f / \{\pi \cdot (\omega 0/2) 2/\lambda\}$ The focal distance f of a human eye is approximately 17 mm, and a maximum beam diameter $\omega 0$ of light that can enter the human eye is approximately 7 mm. Thus, a wavelength required to achieve the spot diameter $\omega 1$ of 2 μm, which enables observation of visual cells, is approximately 650 nm or less. In reality, the spot diameter at the ocular fundus is not equal to the resolution limit, and even a target of 2 μm can be identified with light having the spot diameter $\omega 1$ of, for example, 3 μm if the image has large contrast. In this case, a required wavelength is approximately 970 nm or less.

The above has been calculated assuming that an optical system does not have any aberration. However, in an actual optical system, a distortion in the wavefront that is caused as the light passes through an eyeball needs to be corrected. The Strehl ratio of 0.8 of a beam spot after the wavefront correction is considered to be a diffraction limit, and desired resolution may not be obtained at a Strehl ratio of less than 0.8. The relationship between a Strehl ratio S and a value W of a residual aberration RMS is expressed through the following expression.

$$W=(1-S)^{1/2} \times \lambda/2\pi$$

Accordingly, the Strehl ratio of 0.8 or more corresponds to a situation where the wavelength is 650 nm and the residual aberration RMS is 0.046 μm or less or to a situation where the wavelength is 970 nm and the residual aberration RMS is 0.068 μm or less. However, to date, a reflective optical modulation device that satisfies such performance with an effective diameter suitable for an ophthalmologic apparatus has not existed.

According to an exemplary embodiment of the present invention, a reflective optical modulation device to be used to correct the wavefront is a variable shape mirror having a continuous reflection surface. Such a reflective optical modulation device includes 61 or more actuators within an effective diameter, and each actuator has a stroke length of 7.5 μm or more. Further, the stated effective diameter is 7.5 mm or less. This reflective optical modulation device can yield the Strehl ratio of 0.8 or more after the wavefront correction, and thus desired resolution of the design can be achieved. In addition, the optical system can be reduced in size.

In an ophthalmologic apparatus, light at a distinct wavelength is used depending on a site to be observed or a method for observation. Light in a wavelength band of 850 nm (850 nm±50 nm) that is less affected by being absorbed by water is often used to observe an ocular fundus portion. According to the description on page 8 of N. Doble et al., Applied Optics, Vol. 46, No. 20, 10 Jul. 2007, in order to achieve the Strehl ratio of 0.8 or more with an optical system for light having a beam diameter of 7.5 mm that is incident on a pupil, if the wavelength is 850 nm, the effective diameter of a mirror needs to be divided into nine or more in the radial direction (i.e., 61 or more actuators). Although the wavelength is made shorter in order to achieve higher resolution, light in a visible light range is more likely to cause a subject's viewpoint to move due to an influence of the observation light. Thus, the wavelength of approximately 750 nm or more is preferable, and the number into which the mirror needs to be divided in this case is 10 or more (i.e., 80 or more actuators). In an exemplary embodiment of the present invention, light in a wavelength band of 850 nm, that is, at a maximum of 900 nm or less is used for observation.

Figure 3A:
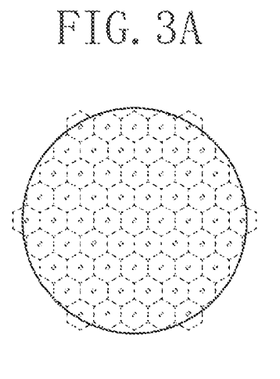
FIGS. 3A to 3F each illustrate an arrangement of actuators in a reflective optical modulation device to be used in an ophthalmologic apparatus of an exemplary embodiment of the present invention.
Figure 3B:
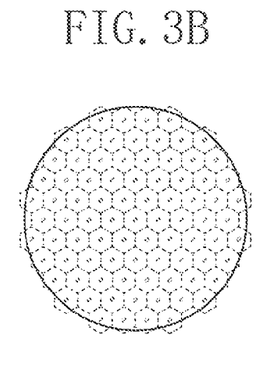
Figure 3C:
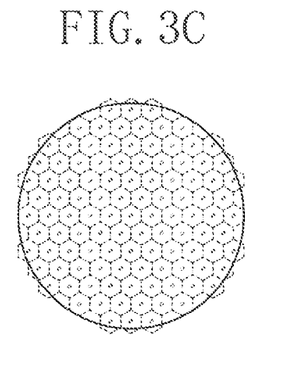
Figure 3D:
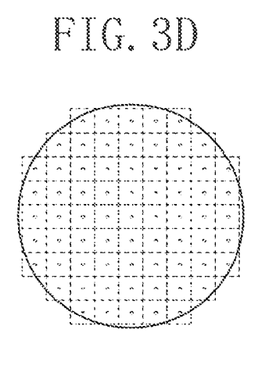
Figure 3E:
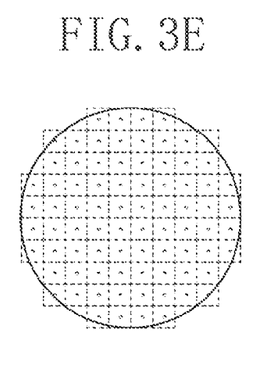
Figure 3F:
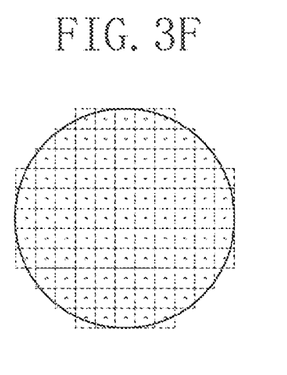

The specific number of actuators within the effective diameter of a variable shape mirror serving as the reflective optical modulation device will now be considered. Here, the variable shape mirror is of a type where a continuous mirror surface is caused to deform. When the actuators are arranged along a two-dimensional plane, typically, a triangular lattice arrangement or a square lattice arrangement as illustrated in FIGS. 3A to 3F can be considered. If the mirror surface within the effective diameter is divided into nine in the radial direction, the number of the actuators arranged in a triangular lattice arrangement turns out to be 61 as illustrated in FIG. 3A, and the number of the actuators arranged in a square lattice arrangement turns out to be 69 as illustrated in FIG. 3D. If the mirror surface within the effective diameter is divided into 10 in the radial direction, the number of the actuators arranged in a triangular lattice arrangement turns out to be 85 as illustrated in FIG. 3B, and the number of the actuators arranged in a square lattice arrangement turns out to be 80 as illustrated in FIG. 3E. If the mirror surface within the effective diameter is divided into 11 in the radial direction, the number of the actuators arranged in a triangular lattice arrangement turns out to be 109 as illustrated in FIG. 3C, and the number of the actuators arranged in a square lattice arrangement turns out to be 97 as illustrated in FIG. 3F.

It is known that in order to obtain the same resolution, a segmented mirror whose segments are driven only to be translated needs to be divided into a number that is 20 times the number of segments of a mirror having a continuous mirror surface that deforms. On the other hand, a segmented mirror whose segments are driven to be translated and tilted about two axes is essentially of the same type as the mirror having a continuous mirror surface that deforms, and thus the same resolution can be obtained with the same number of segments. In exemplary embodiments of the present invention, only a segmented mirror that can be driven to be translated and tilted about two axes is considered as a type of a variable shape mirror having a continuous reflection surface.

Furthermore, according to the description on page 7 of N. Doble et al., Applied Optics, Vol. 46, No. 20, 10 Jul. 2007, a maximum optical path length difference that allows almost any wavefront aberrations of an eye to be corrected is 15 μm or less. A variable shape mirror according to the present exemplary embodiment has a stroke length of 7.5 μm or more. The variable shape mirror is of a reflective type, which makes it possible to correct the aberration of an optical path length difference of 15 μm.

A reflective optical modulation device according to an exemplary embodiment has an effective diameter of 7.5 mm or less. In a case of actuator structures of the existing techniques, if a reflective optical modulation device having a large number of actuators and a large stroke length as described above is to be fabricated, high-density integration of the actuators is difficult, and thus the effective diameter of the reflective optical modulation device becomes large relative to the beam diameter of light incident on a pupil. The effective diameter of the reflective optical modulation device refers to a diameter of an effective region of a variable shape mirror which reflects a light beam and can be set independently of the beam diameter of light incident on the pupil. An optical system of an ophthalmologic apparatus has a configuration in which pupil conjugate positions (wavefront sensor, reflective optical modulation device, scanner, eye pupil) are relayed via respective telescope optical systems. In this configuration, an aberration can more easily be reduced if each telescope optical system has equal magnification. Such a configuration allows a correction residue, which is produced when astigmatism generated by eccentric spherical mirrors is corrected by shifting each of two mirrors in a distinct direction, to be reduced. Since a typical pupil diameter of a human eye is 7 mm or less, if each telescope optical system has equal magnification, it is sufficient that a maximum beam diameter that can be incident on the pupil is approximately 7 mm and the effective diameter of the reflective optical modulation device is 7.5 mm or less including an assembly error. However, to date, it has been difficult to fabricate such a small-sized reflective optical modulation device. Accordingly, if desired aberration correction performance is to be achieved with an existing reflective optical modulation device, the effective diameter becomes as large as 10 mm or more, and thus at least some of the telescope optical systems needs to be constituted by magnifying optical systems. As a result, the optical path length between the reflective optical modulation device and a spherical mirror adjacent to the reflective optical modulation device is increased, which leads to an increase in the size of the optical system, and thus it has been difficult to reduce the optical system in size. Further, astigmatism generated by eccentric spherical mirrors could not be removed sufficiently, and thus it has been difficult to reduce the residual wavefront aberration.

An exemplary embodiment of the present invention can provide a variable shape mirror having a large number of actuators, a large stroke length, and a small effective diameter as described above through the actuator structure described hereinbelow.

A variable shape mirror serving as a reflective optical modulation device according to an exemplary embodiment that realizes the specifications described above will now be described. A preferable actuator structure is such that actuators each formed through a micromachining technique using photolithography are arranged two-dimensionally on a substrate. A comb-shape type actuator structure in which a movable comb-shaped member is interlocked with a fixed comb-shaped member with a space provided therebetween can be employed for a high-density and high-stroke actuator. The movable comb-shaped member is supported by an elastic member to allow the movable comb-shaped member to be displaced in a direction of an optical path, and force is exerted between the movable comb-shaped member and the fixed comb-shaped member. Thus, the movable comb-shaped member is displaced relative to the fixed comb-shaped member. A parallel-plate electrostatic actuator collapses as a movable electrode is pulled into a fixed electrode when a voltage reaches or exceeds a certain value, and thus the stroke cannot be increased. On the other hand, since the comb-shape type actuator structure allows the movable comb-shaped member to move in an in-plane direction of the comb-shaped members, and thus the stroke amount can be increased. The force exerted between the comb-shaped members may be electrostatic force or electromagnetic force. The actuators are connected, through acting units, to a surface of the reflection mirror that is opposite to the reflection surface.

Hereinbelow, an exemplary embodiment of the present invention will be described with reference to the drawings. The present invention, however, is not limited to the examples illustrated herein.

An SLO apparatus will be described as an ophthalmologic apparatus of a first exemplary embodiment of the present invention. In the present exemplary embodiment, an optical aberration of an eye to be examined is corrected using a reflective optical modulation device to obtain a two-dimensional image, which allows a preferable two-dimensional image to be obtained regardless of the diopter or the optical aberration of the eye.

Figure 1:
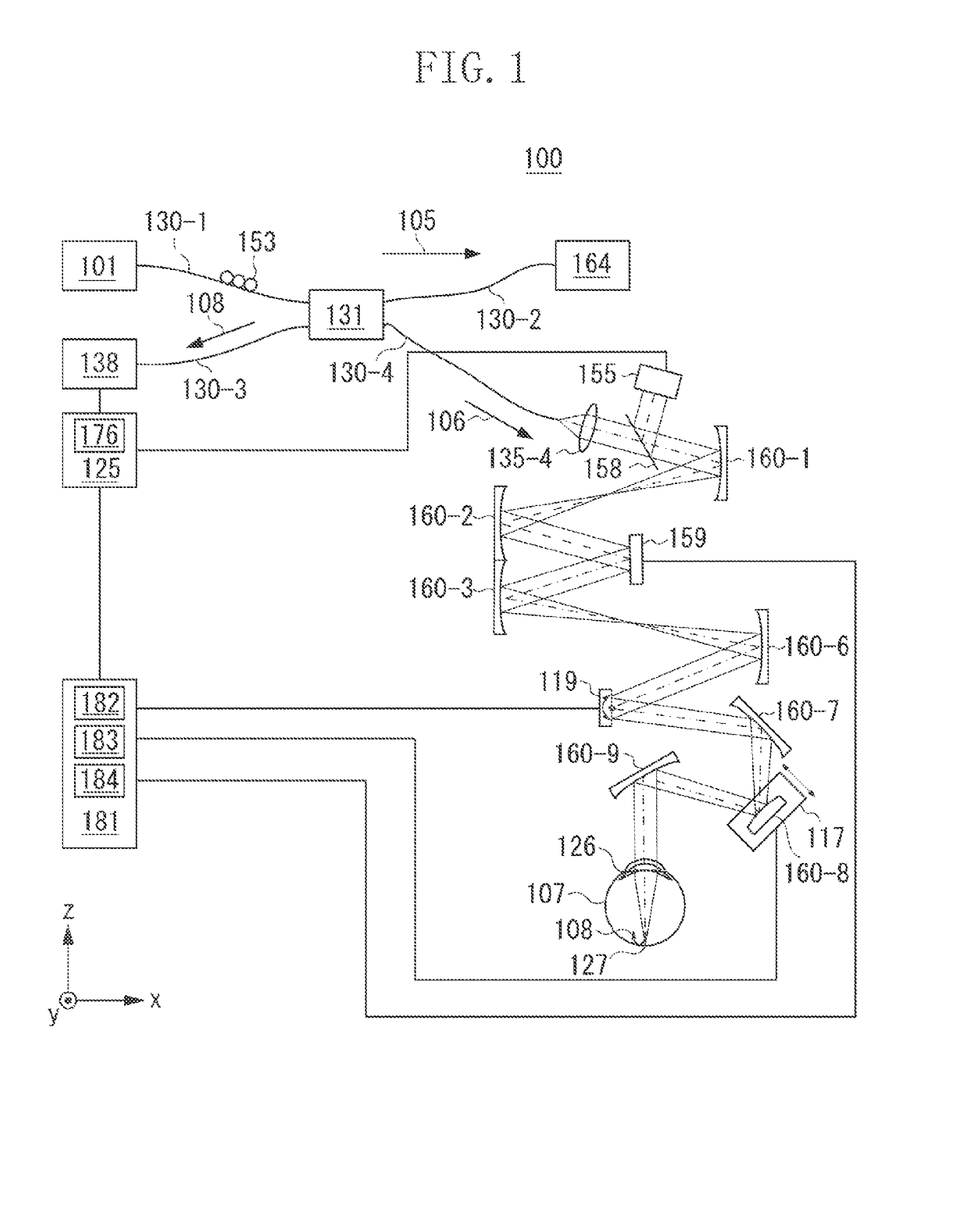
FIG. 1 illustrates an overall configuration of an ophthalmologic apparatus according to a first exemplary embodiment of the present invention.

Referring to FIG. 1, an overall configuration of an SLO apparatus 100 according to the present exemplary embodiment will be described in detail. Light emitted from a light source 101 is split into reference light 105 and measurement light 106 by an optical coupler 131. The measurement light 106 is guided to an eye 107 to be examined through a single mode fiber 130-4, a reflective optical modulation device 159, an XY scanner 119, and spherical mirrors 160-1, 160-2 to 160-3 and 160-6, 160-7, 160-8 to 160-9. The measurement light 106 is reflected or scattered by the eye 107 and, as returning light 108, enters a detector 138. The detector 138 converts the optical intensity of the returning light 108 into a voltage signal, and a two-dimensional image of the eye 107 is formed using the voltage signal. In the present exemplary embodiment, the optical system is constituted generally by a reflective optical system that primarily includes spherical mirrors. Alternatively, the optical system may be constituted by a refractive optical system that includes lenses in place of the spherical mirrors.

The light source 101 and the periphery thereof will now be described. The light source 101 is a superluminescent diode (SLD), which is a typical low coherence light source. The light source 101 emits light at a peak wavelength of 830 nm with a full-with half maximum (FWHM) bandwidth of 50 nm. Here, a low coherence light source is selected in order to obtain a two-dimensional image having less speckle noise. Although an SLD is selected here for the light source 101, the type of the light source 101 is not particularly limited as long as the light source 101 can emit low coherence light, and amplified spontaneous emission (ASE) may also be used.

As for the wavelength, near infrared light is suitable for observing an eye. Furthermore, since the wavelength affects the resolution of an obtained two-dimensional image in the lateral direction, a shorter wavelength is preferable, and the wavelength of 830 nm is employed. Another wavelength may be selected depending on the site to be examined.

The light emitted from the light source 101 is split into the reference light 105 and the measurement light 106 in a ratio of 96 to 4 through a single mode fiber 130-1 and the optical coupler 131. A polarization controller 153 is provided on the single mode fiber 130-1.

The optical path of the reference light 105 will now be described. The reference light 105, which has been split by the optical coupler 131, enters a light amount measurement device 164 through an optical fiber 130-2. The light amount measurement device 164 measures the light amount (e.g., intensity) of the reference light 105 and is used as a light amount monitor of the measurement light 106.

The optical path of the measurement light 106 will now be described. The measurement light 106, which has been split by the optical coupler 131, is guided to a lens 135-4 through a single mode fiber 130-4, and the measurement light 106 is adjusted into parallel light having a beam diameter of 7 mm by the lens 135-4. The measurement light 106 passes through a beam splitter 158, is reflected by the spherical mirrors 160-1 and 160-2, and enters the reflective optical modulation device 159. The reflective optical modulation device 159 is controlled by a computer 125, which serves as a control unit, through a driver 184 in a driver unit 181.

The measurement light 106 is modulated by the reflective optical modulation device 159, is then reflected by the spherical mirrors 160-3 and 160-6, and is incident on a mirror of the XY scanner 119. Although the XY scanner 119 is illustrated here to include a single mirror for the sake of simplicity, in reality, two mirrors, namely an X scanner and a Y scanner are disposed in close proximity to each other to carry out a raster scan on a retina 127 in directions perpendicular to the optical axis. Further, the optical system is adjusted in such way that the center of the measurement light 106 coincides with the rotational center of the mirror of the XY scanner 119.

The X scanner causes the measurement light 106 to scan the retina 127 in a direction parallel to the paper plane, and a resonant scanner is used in the present exemplary embodiment. The drive frequency of the X scanner is approximately 7.9 kHz. The Y scanner causes the measurement light 106 to scan the retina 127 in a direction perpendicular to the paper plane, and a galvanoscanner is used in the present exemplary embodiment. The drive waveform of the Y scanner is a sawtooth wave and has a frequency of 64 Hz and a duty ratio of 16%. The XY scanner 119 is controlled by the computer 125 through an optical scanner driver 182 in the driver unit 181.

The spherical mirrors 160-7 to 160-9 form an optical system for scanning the retina 127 and scans the retina 127 with the measurement light 106 with the vicinity of a cornea 126 serving as a fulcrum.

The SLO apparatus 100 further includes an electric stage 117, and the electric stage 117 can move in directions indicated by an arrow in FIG. 1 to adjust the position of the spherical mirror 160-8 that is attached to the electric stage 117.

The electric stage 117 is controlled by the computer 125 through an electric stage driver 183 in the driver unit 181. Adjusting the position of the spherical mirror 160-8 allows the measurement light 106 to be focused on a predetermined layer in the retina 127 of the eye 107 for observation. The configuration described thus far enables observation even if the eye 107 has ametropia.

Upon entering the eye 107, the measurement light 106 is reflected or scattered by the retina 127, and is turned into the returning light 108. Then, the returning light 108 is guided again to the optical coupler 131 and reaches the detector 138 through a single mode fiber 130-3. A high-speed and high-sensitivity optical sensor such as an avalanche photodiode (APD) or a photomultiplier tube (PMT) is used as the detector 138.

Part of the returning light 108, which has been split by the beam splitter 158, is incident on a Shack-Hartmann wavefront sensor 155, and the aberration of the returning light 108 generated by the eye 107 is measured by the wavefront sensor 155. Accordingly, the wavefront sensor 155 is considered as an aberration measuring unit. The wavefront sensor 155 is electrically connected to the computer 125. The computer 125 serving as the control unit calculates a drive amount of the reflective optical modulation device 159 based on an output of the wavefront sensor 155 and supplies a drive signal to the reflective optical modulation device 159 through the driver 184 to displace actuators. Thus, the computer 125 controls the displacement amount of the reflection mirror of the reflective optical modulation device 159.

Here, the spherical mirrors 160-1 to 160-3 and 160-6 to 160-9 and so on are disposed in such a way that the cornea 126, the XY scanner 119, the wavefront sensor 155, and the reflective optical modulation device 159 are optically conjugate to one another.

Thus, the wavefront sensor 155 can measure the aberration of the wavefront of reflected light 108 reflected from the ocular fundus of the eye 107. Further, the reflective optical modulation device 159, based on the wavefront aberration measured by wavefront sensor 155, can correct the aberration caused by the eye 107.

Furthermore, controlling the reflective optical modulation device 159 in real time based on the aberration obtained from the measurement result of the wavefront sensor 155 makes it possible to correct the aberration generated by the eye 107 and to obtain a two-dimensional image with higher resolution in the lateral direction. In the present exemplary embodiment, the reflective optical modulation device 159 is disposed in the common optical path of the measurement light 106 and the returning light 108, and thus the reflective optical modulation device 159 modulates both the measurement light 106 and the returning light 108 to correct the wavefront aberration of the returning light. The aberration of the measurement light 106 is corrected in order to form an irradiation spot at the fundus, and the aberration of the returning light 108 is corrected in order to form an image of the scattered light from the fundus on the detector 138. In this case, the correction amounts of the aberrations of the measurement light 106 and the returning light 108 are identical since the measurement light 106 and the returning light 108 share the common optical path. Alternatively, one of the measurement light 106 and the returning light 108 may be modulated to correct the wavefront aberration of the returning light. When the measurement light 106 is modulated, the inverse aberration to the aberration obtained by the wavefront sensor 155 is given in advance to the measurement light 106 so that the aberration is cancelled when the measurement light 106 is reflected by the eye 107, to correct the wavefront aberration of the returning light 108. On the other hand, when the returning light 108 is modulated, the aberration caused by the eye 107 is corrected based on the aberration obtained by the wavefront sensor 155, to correct the wavefront aberration of the returning light 108.

Although the spherical mirror 160-8 is used, a cylindrical mirror may be used in place of the spherical mirror 160-8 depending on the aberration (ametropia) of the eye 107. Further, another lens may additionally be disposed in the optical path of the measurement light 106. The optical system of the present exemplary embodiment is constituted of an equal-magnification optical system.

In the present exemplary embodiment, the wavefront sensor 155 measures the aberration using the returning light 108 of the measurement light 106. Alternatively, a dedicated light source may be provided to measure the aberration. Further, another optical path may be formed to measure the aberration. For example, a beam splitter may be provided between the spherical mirror 160-9 and the cornea 126 in order to introduce light into the optical path for measuring the aberration.

The reflective optical modulation device 159 will now be described. A variable shape mirror is used as the reflective optical modulation device 159. The variable shape mirror is configured to allow the mirror shape thereof to deform to generate an optical path length difference in the optical axis direction within the effective diameter.

Figure 2:
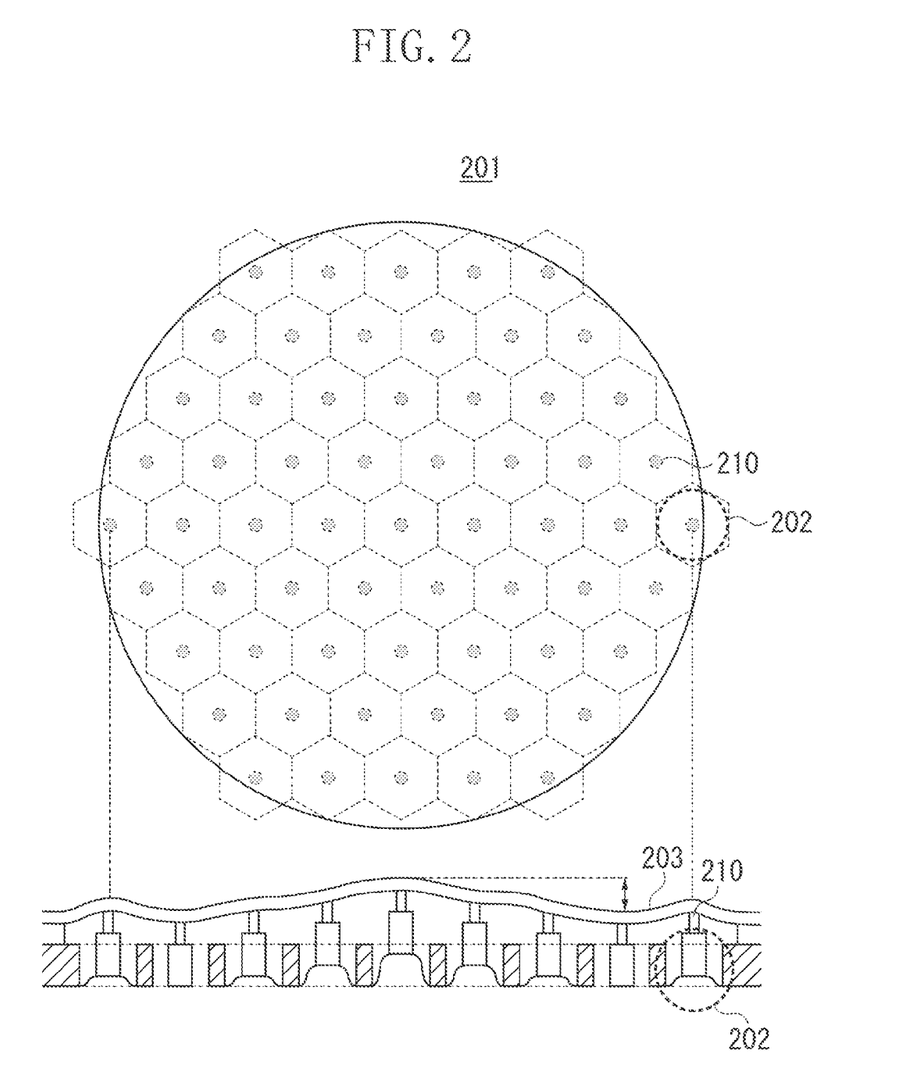
FIG. 2 illustrates a configuration of a reflective optical modulation device to be used in the ophthalmologic apparatus according to the first exemplary embodiment.

Referring to FIG. 2, a variable shape mirror 201 used in the present exemplary embodiment will be described. The upper side of FIG. 2 illustrates an arrangement of actuators within the effective diameter. The lower side of FIG. 2 illustrates a sectional view of the variable shape mirror 201. The drive force generated by each actuator 202 acts on a mirror portion 203 through a corresponding acting unit 210 to deform the mirror portion 203. The variable shape mirror 201 includes 61 actuators 202. Each actuator 202 in a center portion is adjacent to six actuators 202 to form a triangular lattice. The effective diameter of the variable shape mirror 201 is 7.5 mm, distance between the adjacent actuators 202 is 860 µm, and a maximum displacement amount is 10 µm.

Figure 4:
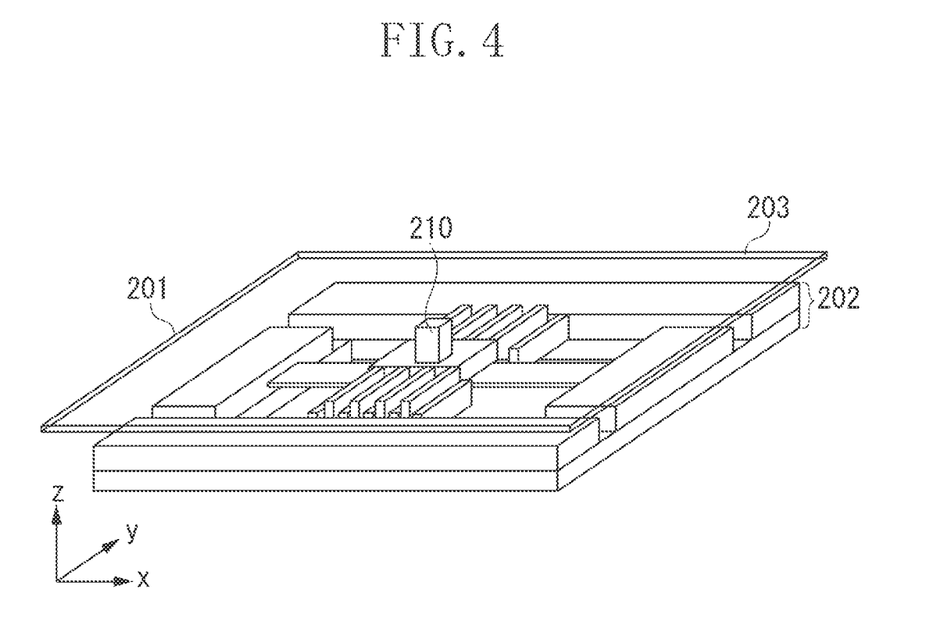
FIG. 4 is a perspective view illustrating a structure of an actuator in the reflective optical modulation device illustrated in FIG. 2.
Figure 5A:
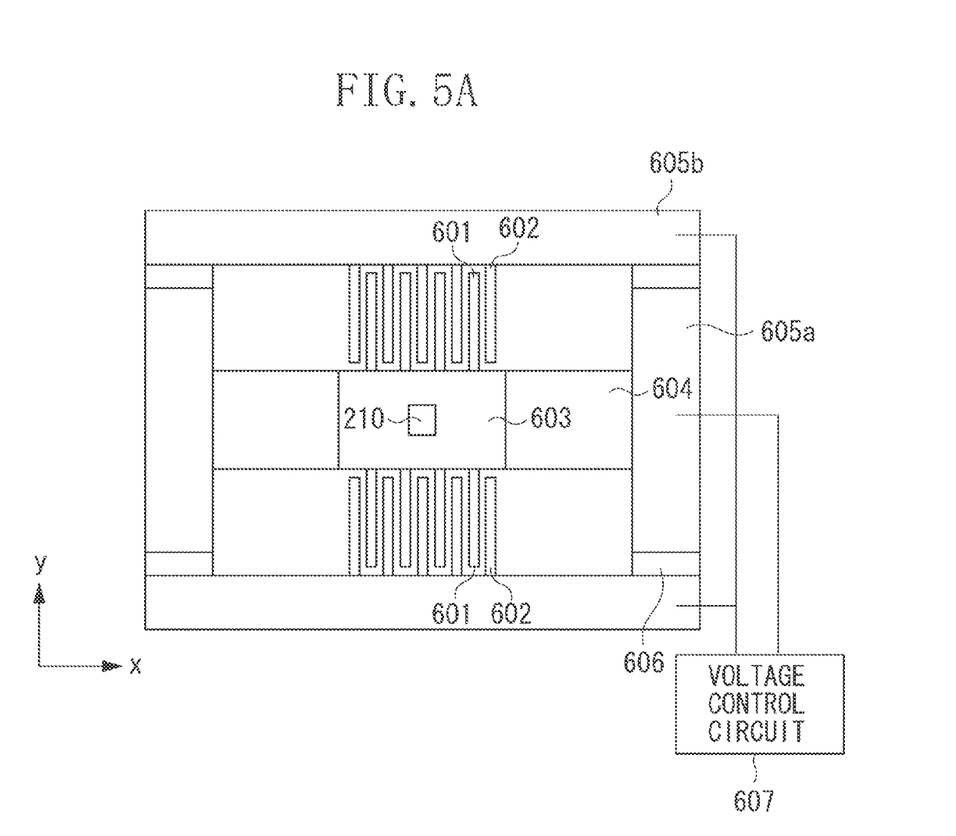
FIG. 5A is a top view of the actuator illustrated in FIG. 4.
Figure 5B:
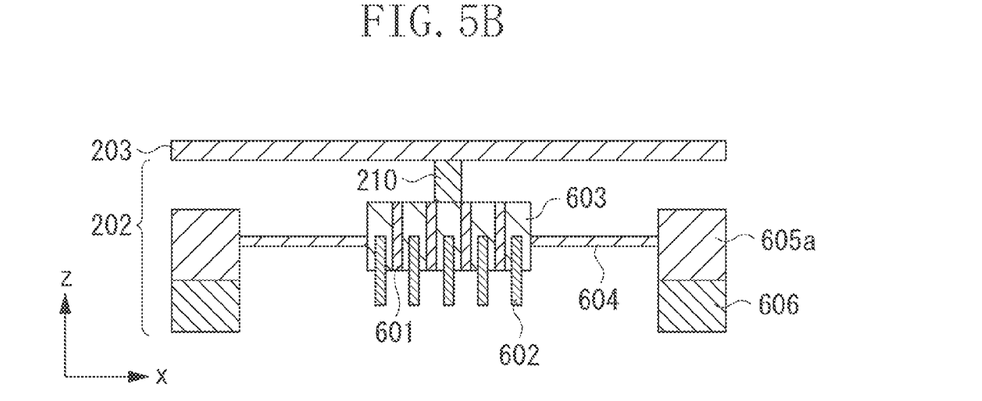
FIG. 5B is a sectional view of the actuator illustrated in FIG. 4.

The variable shape mirror 201 of the present exemplary embodiment is of an electrostatic drive type using comb-shaped electrodes. FIGS. 4, 5A, and 5B illustrates an actuator structure of the variable shape mirror 201 according to the present exemplary embodiment.

In the present exemplary embodiment, the mirror portion 203 (reflection mirror having a reflection surface) is connected to the actuators 202 through respective actuating units 210. Driving the actuators 202 causes the force to act on the acting units 210, and thus the mirror portion 203 deforms.

FIG. 5A is a top view of the actuator 202. In FIG. 5A, the horizontal direction (short side of the paper plane) is defined as an x direction, the vertical direction (long side of the paper plane) is defined as a y direction, and the direction perpendicular to the paper plane is defined as a z direction. An xy plane illustrated in FIG. 5A is substantially parallel to the reflective surface of mirror portion 203. The actuator 202 includes movable comb-shaped electrodes 601, fixed comb-shaped electrodes 602, a movable portion 603, springs 604, support portions 605 (605a, 605b), and the acting unit 210.

The movable portion 603 is connected to the springs 604, the movable comb-shaped electrodes 601, and the acting unit 210. One end of each of the springs 604 is fixed to the support portion 605a.

In the present exemplary embodiment, the movable portion 603 has a shape of a quadrangular prism. The movable comb-shaped electrodes 601 are arranged, respectively, on two side walls among the four side walls of the movable portion 603 which are parallel to an xz plane. The springs 604, which are fixed at one ends to the respective support portions 605a, are connected to the two walls that are parallel to a yz plane.

The acting unit 210 is provided on the upper surface of the movable portion 603 for transmitting the displacement of the movable portion 603 to the mirror portion 203. The movable comb-shaped electrodes 601 are respectively supported at one ends by the side walls of the movable portion 603 that are parallel to the xz plane and extend in a cantilever shape in the y direction (i.e., direction parallel to the reflection surface of the reflection mirror). The fixed comb-shaped electrodes 602 are respectively supported by side walls of the support portions 605b that are parallel to the xz plane and extend in a cantilever shape in the y direction.

Since the side walls of the movable portion 603 oppose the side walls of the support portions 605b, each of the movable comb-shaped electrodes 601 faces a corresponding one of the fixed comb-shaped electrodes 602 in an alternate manner. The sides of the movable comb-shaped electrodes 601 and the sides of the fixed comb-shaped electrodes 602 are disposed at different heights in the z direction (i.e., direction normal to the reflection surface of the reflection mirror), and thus the movable comb-shaped electrodes 601 and the fixed comb-shaped electrodes 602 may overlap only partially.

FIG. 5B is a sectional view of the variable shape mirror 201 and illustrates a positional relationship between the movable comb-shaped electrodes 601 and the fixed comb-shaped electrodes 602 according to the present exemplary embodiment. The movable comb-shaped electrodes 601 are displaced upward relative to the fixed comb-shaped electrodes 602.

Although the depiction is simplified, in the present exemplary embodiment, the movable comb-shaped electrodes 601 include 40 electrode fingers in total and the fixed comb-shaped electrodes 602 include 42 electrode finders in total within a single actuator 202, and thus the total number of gaps between adjacent electrode fingers is 80. Each of the movable comb-shaped electrodes 601 and the fixed comb-shaped electrodes 602 is 200 μm in thickness and 200 μm in length.

The springs 604 extend in the x direction respectively from the side walls of the movable portion 603 that are parallel to the yz plane and are fixed to the side walls of the respective support portions 605a that are parallel to the yz plane. In the present exemplary embodiment, the dimensions of each of the springs 604 are 5 μm in thickness, 500 μm in length in the x direction, and 300 μm in width in the y direction. The fixed comb-shaped electrodes 602 and the springs 604 are fixed by the support portions 605b and 605a, respectively.

Different voltages are applied to the movable comb-shaped electrodes 601 and to the fixed comb-shaped electrodes 602, and thus insulation grooves 606 are provided to electrically insulate between the support portions 605a that are in connection with the movable comb-shaped electrodes 601 and the support portions 605b that are in connection with the fixed comb-shaped electrodes 602. A wire is provided for each of the insulated support portions 605a and 605b to connect the support portions 605a and 605b to a voltage control circuit 607.

The mirror portion 203 is disposed to cover the actuators 202 and is connected to the actuators 202 through the respective acting units 210. With the configuration described above, applying a voltage between the movable comb-shaped electrodes 601 and the fixed comb-shaped electrodes 602 enables the acting unit 210 to displace in the z direction, which is the optical axis direction.

The variable shape mirror 201 is fabricated through a micromachining technique (microelectromechanical system (MEMS) technique) using photolithography. The dimensions of a chip on which the fabricated variable shape mirror 201 is placed are 2 cm×2 cm×0.5 cm (XYZ dimensions).

Figure 6:
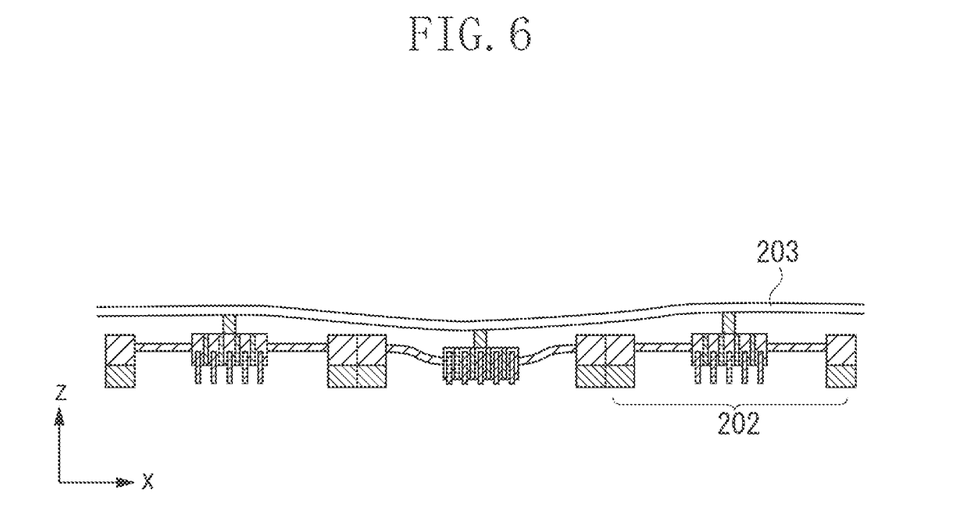
FIG. 6 is a sectional view illustrating a driving state of the actuator illustrated in FIG. 4.

FIG. 6 illustrates a plurality of actuators 202 connected to one another. The mirror portion 203 is disposed to cover the actuators 202 and to form a continuous reflection surface in a reflection region. The shape of the mirror portion 203 can be changed as desired by selectively driving each of the interconnected actuators 202 independently.

Through the actuator structure described thus far, the actuators each having a large stroke amount can be formed in high density.

The configuration of the measurement system will now be described referring back to FIG. 1. The SLO apparatus 100 can obtain a two-dimensional image (SLO image) formed based on the intensity of the returning light 108 from the retina 127. The returning light 108, which is laser light reflected or scattered by the retina 127, enters the detector 138 through the spherical mirrors 160-1 to 160-3 and 160-6 to 160-9, the reflective optical modulation device 159, the optical coupler 131, and so on, and the detector 138 converts the optical intensity of the returning light 108 into a voltage signal.

The voltage signal obtained by the detector 138 is converted into a digital value by an analog to digital (AD) board 176 in the computer 125. Then, the computer 125 carries out data processing in synchronization with the operation and the drive frequency of the XY scanner 119 to form the two-dimensional image. The speed at which the AD board 176 takes in data is 15 MHz.

Part of the returning light 108, which has been split by the beam splitter 158, is incident on the wavefront sensor 155, and the aberration of the returning light 108 is measured therewith. The wavefront sensor 155 is a Shack-Hartmann wavefront sensor. The obtained aberration is expressed through the Zernike polynomial expression, which indicates the aberration of the eye 107. The Zernike polynomial expression includes a tilt term, a defocus term, an astigmatism term, a coma term, and a trefoil term.

A method for obtaining a two-dimensional image (SLO image) will now be described. The SLO apparatus 100 can obtain the two-dimensional image of the retina 127 by controlling the XY scanner 119 to obtain the intensity of the returning light 108 with the detector 138. Upon being incident on the retina 127 through the cornea 126, the measurement light 106 is reflected or scattered by various portions of the retina 127 and is turned into the returning light 108, which then reaches the detector 138.

Detecting the intensities of the returning light 108 while driving the XY scanner 119 in the X direction makes it possible to obtain information at each position along the X axis. In addition, detecting the intensities of the returning light 108 while driving the XY scanner 119 along the X axis and the Y axis simultaneously and carrying out a raster scan on a certain image capturing region of the retina 127 with the measurement light 106 makes it possible to obtain a two-dimensional distribution (two-dimensional image) of the intensities of the returning light 108.

A combined apparatus in which an SLO apparatus and an OCT apparatus are combined will be described as an ophthalmologic apparatus according to a second exemplary embodiment of the present invention. In the present exemplary embodiment, an SLO apparatus that corrects an optical aberration of an eye to be examined by using a reflective optical modulation device and obtains a two-dimensional image is combined with a Fourier domain type OCT apparatus that obtains a tomographic image.

Figure 7:
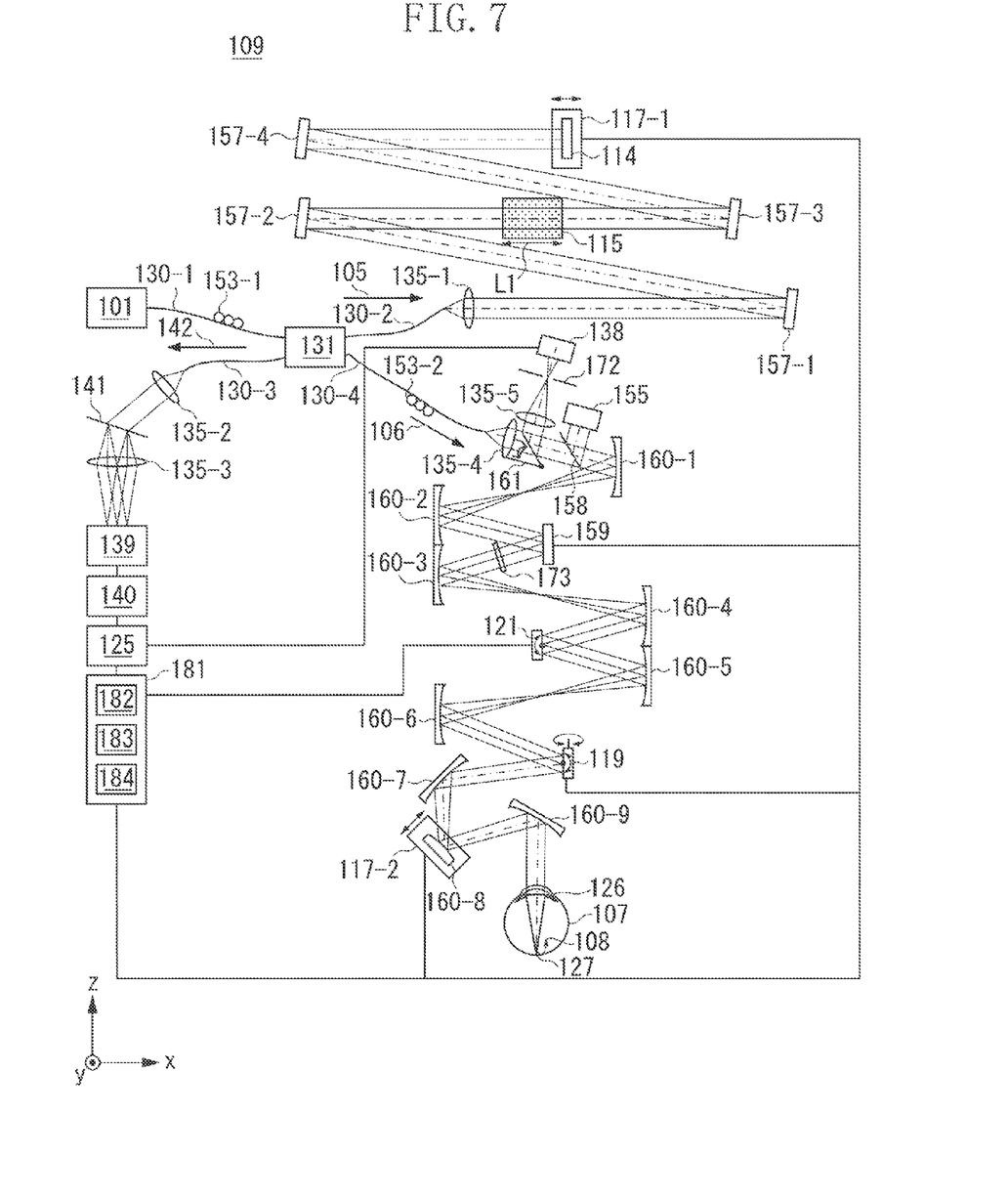
FIG. 7 illustrates an overall configuration of an ophthalmologic apparatus according to a second exemplary embodiment of the present invention.

Referring to FIG. 7, an overall configuration of an ophthalmologic apparatus 109 according to the present exemplary embodiment will now be described in detail. Configurations identical to those of the first exemplary embodiment illustrated in FIG. 1 are given identical reference numerals in FIG. 7, and thus descriptions of portions that are common to the first and present exemplary embodiments will be omitted.

Light emitted from the light source 101 is split into the reference light 105 and the measurement light 106 by the optical coupler 131. The measurement light 106 is guided to the eye 107 to be examined through the single mode fiber 130-4, the reflective optical modulation device 159, the XY scanner 119, an X scanner 121, and spherical mirrors 160-1 to 160-9.

The measurement light 106 is reflected or scattered by the eye 107 and, as the returning light 108, enters the detector 138 or a line camera 139.

The detector 138 converts the optical intensity of the returning light 108 into a voltage signal, and a two-dimensional image of the eye 107 is formed using the voltage signal. The reference light 105 and the returning light 108 are combined (or interfere) with each other and the resulting light enters the line camera 139. Thus, a tomographic image of the eye 107 is formed in the line camera 139. The light source 101 is the same as the light source 101 of the first exemplary embodiment, and thus description thereof will be omitted. An SLD, which is a low coherence light source, is also suitable for capturing a tomographic image.

A reflective optical modulation device having the actuator structure illustrated in FIGS. 2 to 6, which is configured to change the mirror shape thereof to generate an optical path length difference in the optical axis direction within the effective diameter, is used as the reflective optical modulation device 159. Similarly to the one illustrated in FIG. 2, the reflective optical modulation device 159 of the present exemplary embodiment causes the drive force generated by each actuator 202 to act on the mirror portion 203 through a corresponding acting unit 210 to deform the mirror portion 203.

The present exemplary embodiment has the actuator arrangement including 80 actuators 202 as illustrated in FIG. 3E. Each actuator 202 in a center portion is adjacent to four actuators 202 to form a square lattice. The effective diameter of the reflective optical modulation device 159 is 7 mm, distance between the adjacent actuators 202 is 820 µm, and a maximum displacement amount is 8 µm.

The optical path of the reference light 105 will now be described. The reference light 105, which has been split by the optical coupler 131, is guided to a lens 135-1 through the single mode fiber 130-2, and the reference light 105 is adjusted into parallel light having a beam diameter of 7 mm by the lens 135-1.

Then, the reference light 105 is guided to a mirror 114, which serves as a reference mirror, through mirrors 157-1 to 157-4. The optical path length of the reference light 105 is adjusted to substantially coincide with the optical path length of the measurement light 106, and thus the reference light 105 and the measurement light 106 can interfere with each other.

The reference light 105 is then reflected by the mirror 114 and is guided again to the optical coupler 131. A dispersion compensation glass 115, through which the reference light 105 has passed, is provided to compensate an influence on the reference light 105 of optical dispersion caused when the measurement light 106 travels to and from the eye 107.

In the present exemplary embodiment, assuming a representative value as a typical diameter of an eyeball of a Japanese person, L1 is set to 23 mm. The combined apparatus 109 further includes an electric stage 117-1, and the electric stage 117-1 can move in directions indicated by an arrow in FIG. 7 to adjust and control the optical path length of the reference light 105.

The electric stage 117-1 is controlled by the computer 125 through the electric stage driver 183 in the driver unit 181.

The optical path of the measurement light 106 will be described next. The optical system of the present exemplary embodiment is constituted by an equal-magnification optical system. The measurement light 106, which has been split by the optical coupler 131, is guided to the lens 135-4 through the single mode fiber 130-4, and the measurement light 106 is adjusted into parallel light having a beam diameter of 7 mm by the lens 135-4.

A polarization controller 153-1 or 153-2 can adjust the polarization state of the measurement light 106. Here, the measurement light 106 is adjusted to be linearly polarized in a direction parallel to the paper plane. The measurement light 106 passes through a movable beam splitter 161 and the beam splitter 158 and enters the reflective optical modulation device 159 through the spherical mirrors 160-1 and 160-2. The measurement light 106 is then modulated by the reflective optical modulation device 159.

Further, the measurement light 106 passes through a polarization plate 173 and is incident on a mirror of the X scanner 121 through the spherical mirrors 160-3 and 160-4. Here, the polarization plate 173 serves to guide only a polarization component of the returning light 108 that is linearly polarized in a direction parallel to the paper plane to the reflective optical modulation device 159. The X scanner 121 allows the measurement light 106 to scan the retina 127 in a direction parallel to the paper plane, and a resonant scanner is used here.

The drive frequency of the X scanner 121 is approximately 7.9 kHz. Subsequently, the measurement light 106 is incident on a mirror of the XY scanner 119 through the spherical mirrors 160-5 and 160-6. Here, although the XY scanner 119 is illustrated to include a single mirror, in reality, two mirrors, namely an X scanning mirror and a Y scanning mirror are disposed in close proximity to each other.

Further, the optical system is adjusted in such way that the center of the measurement light 106 coincides with the rotational center of the mirror of the XY scanner 119. The drive frequency of the XY scanner 119 can vary within a range up to 500 Hz. The spherical mirrors 160-7 to 160-9 form an optical system for scanning the retina 127 and scans the retina 127 with the measurement light 106 with the vicinity of the cornea 126 serving as a fulcrum.

The combined apparatus 109 further includes an electric stage 117-2, and the electric stage 117-2 can move in directions indicated by an arrow in FIG. 7 to adjust and control the position of the spherical mirror 160-8, which is a spherical mirror attached to the electric stage 117-2. Similarly to the electric stage 117-1, the electric mirror 117-2 is controlled by the electric stage driver 183.

Adjusting the position of the spherical mirror 160-8 enables the measurement light 106 to be focused on a predetermined layer in the retina 127 of the eye 107 for observation. In an initial state, the position of the spherical mirror 160-8 is adjusted so that the measurement light 106 is incident on the cornea 126 as parallel light.

Further, the above configuration enables observation even if the eye 107 has ametropia. Upon entering the eye 107, the measurement light 106 is reflected or scattered by the retina 127 and is turned into the returning light 108. The returning light 108 is then guided again to the optical coupler 131 and reaches the line camera 139.

Part of the returning light 108 is reflected by the movable beam splitter 161 and is guided to the detector 138 through a lens 135-5. The combined apparatus 109 further includes a light blocking plate 172 having a pinhole, and the light blocking plate 172 blocks unnecessary light of the returning light 108 that has not focused on the retina 127.

The light blocking plate 172 is disposed to be conjugate to the focal position of the lens 135-5. The pinhole formed in the light blocking plate 172 is, for example, 50 µm in diameter. A high-speed and high-sensitivity optical sensor such as an APD is used as the detector 138.

Another part of the returning light 108 is split by the beam splitter 158 and enters the wavefront sensor 155. The wavefront sensor 155 is a Shack-Hartmann wavefront sensor. Here, the spherical mirrors 160-1 to 160-9 are disposed so that the XY scanner 119, the X scanner 121, the cornea 126, the wavefront sensor 155, and the reflective optical modulation device 159 are optically conjugate to one another.

Thus, the wavefront sensor 155 can measure the aberration of the eye 107. Further, the reflective optical modulation device 159 can correct the aberration of the eye 107. Controlling the displacement amount of the reflection mirror of the reflective optical modulation device 159 in real time based on the obtained aberration makes it possible to correct the aberration generated by the eye 107 and to obtain a tomographic image having higher resolution in the lateral direction.

The configuration of the measurement system will now be described. The combined apparatus 109 can obtain a tomographic image (OCT image) and a two-dimensional image (SLO image).

The measurement system for a tomographic image will be described first. The optical coupler 131 combines (or interfere) the returning light 108 with the reference light 105. Combined (interfered with) light 142 is guided to a transmissive grating 141 through the single mode fiber 130-3 and a lens 135-2 and is spectrally divided in accordance with the wavelengths by the transmissive grating 141. The resulting light 142 then enters the line camera 139 through a lens 135-3.

The line camera 139 converts the optical intensity obtained at each position (i.e., for each wavelength) into a voltage signal. The voltage signal is then converted into a digital value by a frame grabber 140, and a tomographic image of the eye 107 is formed by the computer 125. The line camera 139 includes 1024 pixels and can obtain the intensity of the combined (interfered with) light 142 for each wavelength (1024 blocks).

The measurement system for a two-dimensional image will now be described. Part of the returning light 108 is reflected by the movable beam splitter 161. The light blocking plate 172 blocks unnecessary light of the reflected light, and the resulting light reaches the detector 138, with which the optical intensity is converted into an electrical signal.

The computer 125 carries out data processing on the obtained electrical signal in synchronization with scan signals for the X scanner 121 and the XY scanner 119, and thus a two-dimensional image is formed. Another part of the returning light 108 is split by the beam splitter 158 and enters the wavefront sensor 155, with which the aberration of the returning light 108 is measured.

An image signal obtained by the wavefront sensor 155 is taken into the computer 125, with which the aberration is calculated. The obtained aberration is expressed through the Zernike polynomial expression, which indicates the aberration of the eye 107. The Zernike polynomial expression includes a tilt term, a defocus term, an astigmatism term, a coma term, and a trefoil term.

Subsequently, a method for obtaining a tomographic image (OCT image) using the combined apparatus 109 will be described.

The combined apparatus 109 controls the XY scanner 119 to obtain interference fringes by the line camera 139 with the X scanner 121 serving as a fixed mirror. Thus, the combined apparatus 109 can obtain a tomographic image of the retina 127. The movable beam splitter 161 is controlled so that the returning light 108 is not guided to the detector 138.

The X scanner 121 and the XY scanner 119 are controlled by the computer 125 through the optical scanner driver 182 in the driver unit 181. Here, a method for obtaining a tomographic image of the retina 127 (along a plane parallel to the optical axis) will be described.

Upon being incident on the retina 127 through the cornea 126, the measurement light 106 is reflected or scattered by various portions of the retina 127 and is turned into the returning light 108. Then, the returning light 108 enters the line camera 139 with a temporal delay generated at various positions. Here, since the light source 101 has a broad bandwidth and a small coherence length, if the optical path length of the reference light 105 is substantially equal to the optical path length of the measurement light 106, interference fringes can be detected by the line camera 139. As described above, the line camera 139 obtains the interference fringes in a spectral range along a wavelength axis.

Subsequently, the interference fringes, which indicate information on the wavelength axis, are converted into interference fringes of an optical frequency axis with the characteristics of the line camera 139 and the transmissive grating 141 taken into consideration. The converted interference fringes of the optical frequency axis are subjected to the inverse Fourier transform to obtain information in the depth direction. Further, detecting the interference fringes while driving the XY scanner 119 makes it possible to obtain interference fringes at a plurality of positions along the X axis. That is, information in the depth direction at each position along the X axis can be obtained.

As a result, a two-dimensional distribution (tomographic image) of the intensities of the returning light 108 along the xz plane can be obtained.

Subsequently, a method for obtaining a two-dimensional image (SLO image) using the combined apparatus 109 will be described.

The combined apparatus 109 can obtain the two-dimensional image of the retina 127 by operating and controlling the XY scanner 119 only in the Y axis direction and the X scanner 121 while the XY scanner 119 is fixed in the X axis direction, and by obtaining the intensity of the returning light 108 with the detector 138.

At this point, a blocking member (not illustrated) is placed in the optical path of the reference light 105 so that returning light of the reference light 105 does not return to the optical coupler 131. The X scanner 121 and the XY scanner 119 are controlled by the computer 125 through the optical scanner driver 182 in the driver unit 181.

The combined apparatus 109 controls the reflective optical modulation device 159 based on the aberration of the eye 107 measured by the wavefront sensor 155 and thus can obtain a two-dimensional image while correcting the aberration generated by the eye 107 and so on. The combined apparatus 109 can obtain the two-dimensional image while controlling the reflective optical modulation device 159 in real time. The specific method for obtaining the two-dimensional image is similar to that of the first exemplary embodiment, and thus description thereof will be omitted.

According to the ophthalmologic apparatus according to the present exemplary embodiment, the resolution of approximately 2 μm can be obtained for a larger number of eyes, and thus detailed observation of an ocular fundus including observation of a rod cell, a cone cell of a central fovea in the macular area, an optic nerve, and a peripheral blood flow becomes possible. In particular, early detection of ocular fundus diseases such as cone dystrophy or Stargardt's disease where an abnormality occurs in the cone cells in the macular area, retinitis pigmentosa where an abnormality occurs primarily in the rod cells, glaucoma where the optic nerves undergo atrophy, and diabetic retinopathy or branch retinal vein occlusion where an abnormality occurs in the peripheral blood flow becomes possible.

Furthermore, since the effective diameter of the reflection mirror is equal to or less than 7.5 mm, the reflective optical modulation device can be reduced in size, and therefore the optical system can be reduced in size.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2012-239285 filed Oct. 30, 2012, which is hereby incorporated by reference herein in its entirety.

What is claimed is:

1. An ophthalmologic apparatus configured to obtain an image of an eye to be examined, the ophthalmologic apparatus comprising:
   an aberration measuring unit configured to measure aberration of returning light;
   a reflective optical modulation device configured to modulate at least one of a measurement light and the returning light; and
   a control unit configured to control the reflective optical modulation device based on a measurement result obtained by the aberration measuring unit,
   wherein the reflective optical modulation device includes:
   a reflection mirror having an effective diameter of 7.5 mm or less, and
   61 or more actuators that act on the reflection mirror within the effective diameter of 7.5 mm or less, the actuators having a stroke length of 7.5 µm or more in a direction intersecting a reflection surface of the reflection mirror.

2. The ophthalmologic apparatus according to claim 1, wherein the actuator includes:
   a movable portion being connected to the reflection mirror;
   a spring supported by the movable portion;
   a support portion supporting the movable portion via the spring;
   a plurality of movable comb-shaped electrodes supported by the movable portion and extending from the movable portion to the support portion;
   a plurality of fixed comb-shaped electrodes supported by the support portion, extending from the movable portion to the support portion, and disposed alternately with the movable comb-shaped electrodes; and
   a voltage control unit configured to apply a voltage between the movable comb-shaped electrode and the fixed comb-shaped electrode to displace the movable comb-shaped electrode and the movable portion in a direction which intersects a direction in which the movable comb-shaped electrodes and the fixed comb-shaped electrodes are alternately arranged and intersects a direction in which the movable comb-shaped electrodes extend from the movable portion to the support portion.

3. The ophthalmologic apparatus according to claim 2,
   wherein the movable comb-shaped electrode is supported by the movable portion in a cantilever state, and
   wherein the fixed comb-shaped electrode is supported by the support portion in a cantilever state.

4. The ophthalmologic apparatus according to claim 1, wherein the reflection surface of the reflection mirror is continuous within the effective diameter.

5. The ophthalmologic apparatus according to claim 1, further comprising a light source configured to emit laser light.

6. The ophthalmologic apparatus according to claim 1, wherein the aberration measuring unit is a Shack-Hartmann wavefront sensor.

7. The ophthalmologic apparatus according to claim 5, further comprising an optical system configured to guide the laser light emitted from the light source to the eye as the measurement light,
   wherein the optical system is formed by connecting equal-magnification telescope optical systems.

8. The ophthalmologic apparatus according to claim 7, wherein the equal-magnification telescope optical systems also serve as an optical system for guiding the returning light from the eye to the aberration measuring unit.

9. The ophthalmologic apparatus according to claim 8, wherein a cornea of the eye, the aberration measuring unit, and the reflective optical modulation device are arranged to be optically conjugate to one another.

10. The ophthalmologic apparatus according to claim 1, wherein the reflective optical modulation device includes 80 or more actuators that act on the reflection mirror within the effective diameter of 7.5 mm or less.

11. The ophthalmologic apparatus according to claim 1, wherein the ophthalmologic apparatus includes a scanning laser ophthalmoscope apparatus.

12. The ophthalmologic apparatus according to claim 1, wherein the ophthalmologic apparatus includes a combined apparatus of an optical coherence tomography apparatus and a scanning laser ophthalmoscope apparatus.

13. The ophthalmologic apparatus according to claim 1,
   wherein the reflection surface of the reflection mirror is consecutive across the effective diameter.

14. The ophthalmologic apparatus according to claim 1,
   wherein the reflection surface of the reflection mirror is continuous across the effective diameter.

15. The ophthalmologic apparatus according to claim 1,
   wherein the reflection surface of the reflection mirror is serial across the effective diameter.

16. The ophthalmologic apparatus according to claim 1,
   wherein the reflection mirror is connected to an actuator via an actuating unit, and
   wherein a number of actuating units arranged on the reflection mirror within the effective diameter is same as a number of actuators on the reflection mirror within the effective diameter.

17. The ophthalmologic apparatus according to claim 1, wherein the stroke length has a maximum displacement of 8 µm.

18. The ophthalmologic apparatus according to claim 1, wherein the stroke length has a maximum displacement of 10 µm.

19. The ophthalmologic apparatus according to claim 1, wherein the actuator includes:
   a movable portion being connected to the reflection mirror;
   a spring supported by the movable portion;
   a support portion supporting the movable portion via the spring;
   a plurality of movable comb-shaped electrodes comprising a first group supported by a first surface of the movable portion and a second group supported by a second surface different from the first surface of the movable portion;
   a plurality of fixed comb-shaped electrodes comprising a third group supported by a third surface of the support portion and a fourth group supported by a fourth surface different from the third surface of the support portion; and
   a voltage control unit configured to apply a voltage between the movable comb-shaped electrodes and the fixed comb-shaped electrodes.

20. The ophthalmologic apparatus according to claim 19, wherein the movable comb-shaped electrodes in the first group and the fixed comb-shaped electrodes in the third group are alternately arranged, wherein the movable comb-shaped electrodes in the second group and the fixed comb-shaped electrodes in the fourth group are alternately arranged, and wherein the voltage control unit is configured to apply a voltage between the movable comb-shaped electrodes and the fixed comb-shaped electrodes so that a potential of the fixed comb-shaped electrodes in the third group is substantively equal to a potential of the fixed comb-shaped electrodes in the fourth group.

21. The ophthalmologic apparatus according to claim 20, wherein the voltage control unit is configured to apply a voltage between the movable comb-shaped electrodes and the fixed comb-shaped electrodes so that a potential of the movable comb-shaped electrodes in the first group is substantively equal to a potential of the movable comb-shaped electrodes in the second group.

22. An ophthalmologic apparatus configured to obtain an image of an eye to be examined, the ophthalmologic apparatus comprising:

an aberration measuring unit configured to measure aberration of returning light;

a reflective optical modulation device configured to modulate at least one of a measurement light and the returning light; and a control unit configured to control the reflective optical modulation device corresponding to a measurement result obtained by the aberration measuring unit, wherein the reflective optical modulation device includes a reflection mirror having an effective diameter of 7.5 mm or less, and 61 or more actuators that act on the reflection mirror within the effective diameter of 7.5 mm or less, the actuator being configured to be able to be displaced by 7.5 μm or more in a direction intersecting a reflection surface of the reflection mirror.

* * * * *